United States Patent
Darcey

(10) Patent No.: US 6,478,760 B2
(45) Date of Patent: Nov. 12, 2002

(54) CUSTOM MOLDED TENNIS ELBOW PAD ASSEMBLY

(75) Inventor: Thomas D. Darcey, Mooresville, NC (US)

(73) Assignee: BSN Medical Inc., Wilmington, DE (US)

( * ) Notice: Subject to any disclaimer, the term of this patent is extended or adjusted under 35 U.S.C. 154(b) by 0 days.

(21) Appl. No.: 09/726,943

(22) Filed: Nov. 30, 2000

(65) Prior Publication Data

US 2002/0099316 A1 Jul. 25, 2002

(51) Int. Cl.[7] .................................................. A61F 5/00
(52) U.S. Cl. .................................. 602/20; 602/1; 602/5; 602/6; 602/8
(58) Field of Search .............................. 602/13–14, 20, 602/21, 23, 26, 60, 61, 62, 63, 79, 1, 5, 8, 6; 2/16

(56) References Cited

U.S. PATENT DOCUMENTS

| 3,586,001 | A |   | 6/1971  | Sanderson |         |
|-----------|---|---|---------|-----------|---------|
| 4,014,327 | A |   | 3/1977  | Spiro     |         |
| 4,243,028 | A |   | 1/1981  | Puyana    |         |
| 4,628,918 | A |   | 12/1986 | Johnson, Jr. |      |
| 4,888,225 | A |   | 12/1989 | Sandvig et al. |    |
| 4,893,617 | A |   | 1/1990  | Bartial et al. |    |
| 5,152,302 | A |   | 10/1992 | Fareed    |         |
| 5,165,402 | A |   | 11/1992 | McCoy     |         |
| 5,295,951 | A |   | 3/1994  | Fareed    |         |
| 5,334,442 | A | * | 8/1994  | Okamoto et al. | 442/224 |
| 5,480,376 | A | * | 1/1996  | Duback et al. |     |
| 5,732,713 | A | * | 3/1998  | Duback et al. |     |
| 5,755,678 | A | * | 5/1998  | Parker et al. | 602/6 |
| 5,971,947 | A |   | 10/1999 | McNally et al. |    |
| 6,027,777 | A |   | 2/2000  | Hirano et al. |     |
| 6,128,777 | A | * | 10/2000 | Foreman   |         |

FOREIGN PATENT DOCUMENTS

| EP | 0 934 749 A1 | 12/1998 |
| WO | WO 00/33772  | 6/2000  |

* cited by examiner

Primary Examiner—Michael A. Brown
Assistant Examiner—Lalita M Hamilton
(74) Attorney, Agent, or Firm—Adams, Schwartz & Evans, P.A.

(57) ABSTRACT

A tennis elbow pad assembly product for relieving the symptoms of lateral epicondylitis is disclosed. The tennis elbow pad assembly product includes an outer pouch formed of a moisture-impervious material. A pad is positioned in the pouch in substantially moisture-free conditions and sealed therein against entry of moisture until use. The pad is adapted for being positioned against and molded onto a forearm in the region of the elbow for lying in closely-conforming relation against and applying radially-directed pressure to the common tendon attachment and grasping and supination muscles associated with the radial-humeral joint and the lateral epicondyle of a forearm and hardened into a rigid structure for therapeutic use. The pad includes an initially flexible substrate impregnated or coated with a reactive system. The system remains stable when maintained in substantially moisture-free conditions and hardens upon exposure to moisture to form a rigid, self-supporting structure having a shape that conforms to the forearm to which the pad is molded during curing. The pad also includes a flexible outer layer enclosing the substrate and a support cooperating with the pad for maintaining the pad in its closely-conforming position against the forearm.

33 Claims, 9 Drawing Sheets

CUSTOM MOLDED TENNIS ELBOW PAD ASSEMBLY

TECHNICAL FIELD AND BACKGROUND OF THE INVENTION

This invention relates to a custom-molded pad for relief of the symptoms of lateral epicondylitis, or "tennis elbow." Also known as tendonitis or tenosenonitis, tennis elbow is the inflammation of the tendon or tendon sheath located at the lateral epicondyle. Tennis elbow is primarily caused by continued stress on the grasping and supination muscles of the forearm. Although the backhand swing in tennis is an activity commonly associated with aggravating the onset of lateral epicondylitis, there are several other activities that can cause the condition, such as continuous use of hand tools, repetitive painting with a brush or roller, or carrying and operating a chain saw over extended periods of time. As discussed below, each of these activities require repeated use of the same muscle groups, which often leads to overuse and the inflammation and tearing associated with tennis elbow.

Although some severe or chronic cases of tennis elbow may require use of anti-inflammatory drugs or surgical intervention, the vast majority of cases are resolved using much simpler methods. Standard treatment for a typical case of tennis elbow involves little more than applying ice to and resting the affected area, and alleviating any associated pain. In many cases, an external device will also be used to support the affected muscles and tendons during normal activities, thereby reducing the risk of further injury while allowing time for the damaged area to heal.

While prompt diagnosis and treatment of lateral epicondylitis can minimize the pain associated with the condition and reduce the extent of treatment needed, prior art methods available for treatment often fail to provide adequate relief. A typical external elbow wrap used to treat tennis elbow consists of nothing more than an elastic strap which extends around the forearm. This type of prior art strap does not provide concentrated support directly over the injured area. Those devices which do attempt to direct support specifically to the injured region have limited effectiveness in that they provide additional padding over the inflamed area, yet fail to provide a secure, custom fit which addresses the unique anatomical needs of the individual wearer. Furthermore, the additional padding provided is often a soft, thick foam pad, which will not conform to the shape of the forearm without applying an increased amount of pressure over the injured area to cause the foam to compress against the forearm.

The tennis elbow band of the present invention offers an improved alternative to conventional elastic bands and ice packs by providing a custom-fitted pad which is molded to conform to the exact shape of the anatomy of the wearer. The pad is first placed over the wearer's forearm and cured to a custom-fitted shape, and is then secured over the inflamed area of the forearm using an adjustable strap. The strap and the pad cooperate with one another to provide a custom-fitted device that produces concentrated, radially-directed support to the injured muscles and tendons. Unlike some prior art pads, the pad of the present invention does not require the use of thick layer of foam padding to provide adequate support to the injured area, but instead relies upon layers of rigid, resin-impregnated fabric. This results in a thin pad against which a reduced amount of radially-directed pressure must be applied to achieve a greater degree of support. This promotes blood flow to the injured area and accelerates the healing process.

The tennis elbow band of the present invention uses a moisture curable resin system to quickly and easily mold the pad to the shape of the muscles and tendons of the forearm. Upon curing, the moisture curable resin system yields a very rigid pad having a custom-fitted shape that matches the area of the forearm to which the pad was initially molded. No heat is required. A source of water is the only additional material necessary to achieve a cure. Although atmospheric moisture alone will cure the tennis elbow pad into its hardened position in a relatively short period of time, the resin in or on the pad will typically be activated by immersing the pad in water prior to fitting the pad on an individual's forearm. Even though atmospheric moisture can activate the curing process, once a final cure is achieved, the tennis elbow pad will maintain its custom-fitted shape regardless of whether the pad is subsequently exposed to heat or moisture. The tennis elbow pad assembly is inexpensive to produce, easy to fabricate, and comfortable to wear.

SUMMARY OF THE INVENTION

Therefore, it is an object of the invention to provide a custom-molded tennis elbow pad assembly that can be quickly and easily positioned on and removed from a wearer's forearm by the wearer.

It is another object of the invention to provide a tennis elbow pad assembly which is easy to fabricate.

It is another object of the invention to provide a tennis elbow pad having a universal size and a standard shape prior to being custom-fitted to a wearer's forearm.

It is another object of the invention to provide a tennis elbow pad that hardens in the presence of moisture to form a very rigid yet very lightweight protective pad.

It is another object of the invention to provide a tennis elbow pad that is stored in a moisture-proof pouch until ready for application to the forearm muscles and tendons to be supported.

These and other objects of the present invention are achieved in the preferred embodiments disclosed below by providing a tennis elbow pad assembly product for relieving the symptoms of lateral epicondylitis. The tennis elbow pad assembly product includes an outer pouch formed of a moisture-impervious material. A pad is positioned in the pouch in substantially moisture-free conditions and sealed therein against entry of moisture until use. The pad is adapted for being positioned against and molded onto a forearm in the region of the elbow for lying in closely-conforming relation against and applying radially-directed pressure to the common tendon attachment and grasping and supination muscles associated with the radial-humeral joint and the lateral epicondyle of a forearm and hardened into a rigid structure for therapeutic use. The pad includes an initially flexible substrate impregnated or coated with a reactive system. The system remains stable when maintained in substantially moisture-free conditions and hardens upon exposure to moisture to form a rigid, self-supporting structure having a shape that conforms to the forearm to which the pad is molded during curing. The pad also includes a flexible outer layer enclosing the substrate and a support cooperating with the pad for maintaining the pad in its closely-conforming position against the forearm.

According to one preferred embodiment of the invention, the support is an elongate strap having an outer surface and first and second ends. The first end of the strap is attached to the pad, thereby permitting the strap to extend around the forearm. The strap may then be releasably attached to an upper surface of the pad for securing the pad in the supporting position against the forearm.

According to another preferred embodiment of the invention, outer moisture-proof pouch is formed of a laminated structure having at least one layer of plastic film and at least one layer of aluminum foil bonded to said plastic film.

According to yet another preferred embodiment of the invention, the inner layer includes a plurality of overlaid thicknesses of fiberglass.

According to yet another preferred embodiment of the invention, the plurality of overlaid thicknesses includes at least three and no more than five thicknesses.

According to yet another preferred embodiment of the invention, the outer layer includes an innermost foam layer overlying at least one side of the substrate.

According to yet another preferred embodiment of the invention, the outer layer comprises an innermost foam layer enclosing the substrate therein.

According to yet another preferred embodiment of the invention, foam layer is selected from the group consisting of closed-cell ethylene vinyl acetate and polyurethane.

According to yet another preferred embodiment of the invention, the outer layer also includes a flexible protective cover enclosing the foam layer. The substrate, foam layer and cover are joined together to form a unitary structure for being molded while flexible to an aspect of the forearm and elbow.

According to yet another preferred embodiment of the invention, the cover is formed of a polyester sheeting fabric.

According to yet another preferred embodiment of the invention, the reactive system includes a blended polyisocyanate, polyol, catalyst and stabilizer.

According to yet another preferred embodiment of the invention, the tennis elbow pad assembly includes a loop attached to said upper surface and adapted for receiving the strap therethrough for securing the pad against the forearm.

According to yet another preferred embodiment of the invention, the tennis elbow pad assembly includes a first fastener attached to the upper surface for cooperating with a complementary second fastener attached to the strap for holding the pad in place on the forearm while being worn.

According to yet another preferred embodiment of the invention, one of the first and second fasteners is patch of looped material, and the other of the first and second fasteners is a complementary patch of hooked material.

According to yet another preferred embodiment of the invention, the first end of the strap includes a fastening ring connected thereto and adapted for receiving the second end therethrough for securing the strap around the forearm.

According to yet another preferred embodiment of the invention, the tennis elbow pad assembly product includes a third fastener attached to the second end of the strap for being releasably connected to the outer surface, thereby permitting the strap to be secured around the forearm.

According to yet another preferred embodiment of the invention, the surface of the strap is formed from hook-and-loop material.

According to yet another preferred embodiment of the invention, the third fastener is a patch of hook-and-loop material complementary to the outer surface.

According to yet another preferred embodiment of the invention, a tennis elbow pad assembly for relieving the symptoms of lateral epicondylitis is provided. The tennis elbow pad assembly includes a pad adapted for being positioned against and molded onto a forearm in the region of the elbow for lying in closely-conforming relation against and applying radially-directed pressure to the common tendon attachment and grasping and supination muscles associated with the radial-humeral joint and the lateral epicondyle of a forearm. The pad is hardened into a rigid structure for therapeutic use, and includes an initially flexible inner substrate impregnated or coated with a reactive system. The system remains stable when maintained in substantially moisture-free conditions and hardens upon exposure to moisture to form a rigid, self-supporting structure having a shape conforming to the forearm to which the pad is molded during curing. The pad also includes a flexible cover enclosing the substrate. A support cooperates with the pad for maintaining the pad in its closely-conforming position against the forearm.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND THE BEST MODE

Figure 1:
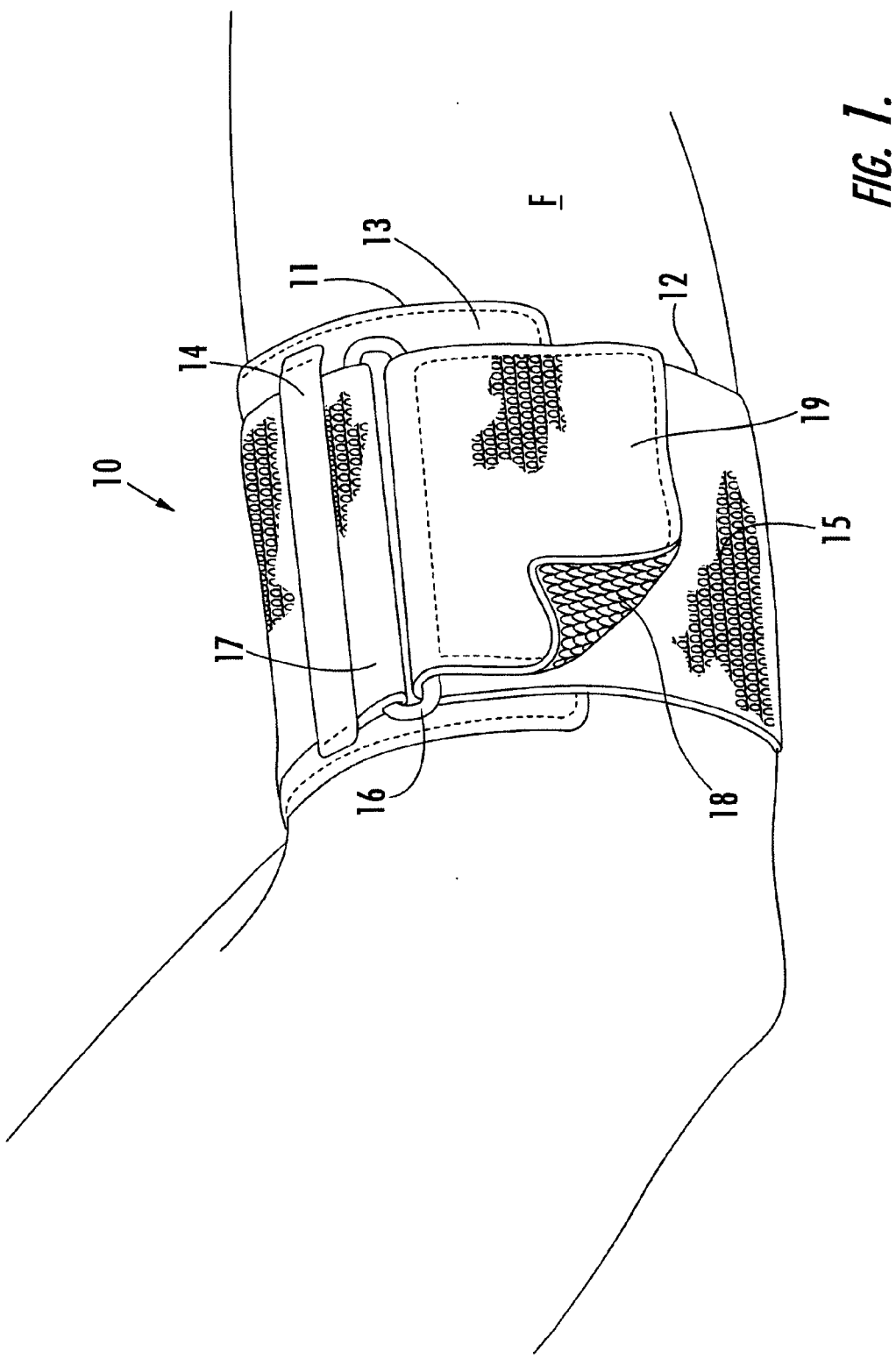
FIG. 1 is an environmental perspective view of a tennis elbow pad assembly according to one embodiment of the invention showing the manner in which the tennis elbow pad is releasably secured around a forearm.

Referring now specifically to the drawings, a tennis elbow pad assembly is illustrated in FIG. 1 and shown generally at reference numeral 10. The assembly 10 includes a pad 11 which, as is described in detail below, is custom-fitted to a wearer's forearm "F", and is held in place by an elongate strap 12. The pad 11 has an upper surface 13 to which the ends of a relatively narrow strap loop 14 are sewn. The loop 14 extends across the pad 11 and maintains the strap 12 in place around the forearm "F". The strap 12 is preferably formed of a narrow length of woven or knitted material having surfaces formed from a loose fibrous covering 15. A D-ring 16 is secured to a first end 17 of the strap 12, and a first patch of hook material 18 is sewn, glued, or otherwise connected to a second end 19. The strap 12 is formed into a loop around the forearm "F" by passing the strap 12 through the D-ring 16. The pad 11 is then secured against the forearm "F" by pulling the strap 12 so that the pad 11 fits closely against the forearm "F" and securing the patch of hook material 18 to the fibrous covering 15 at the desired position.

Figure 2:
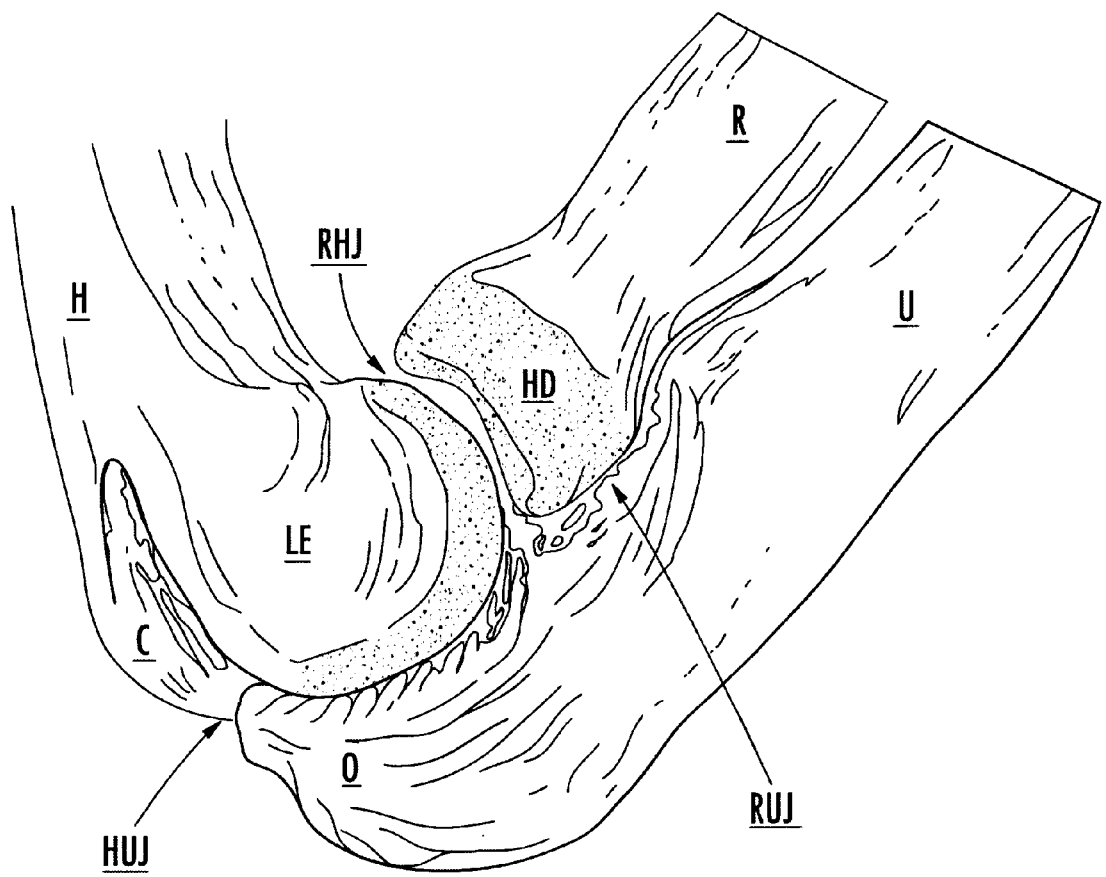
FIG. 2 is a perspective view of the bones and joints of the right elbow of a human during flexion of the elbow.
Figure 3A:
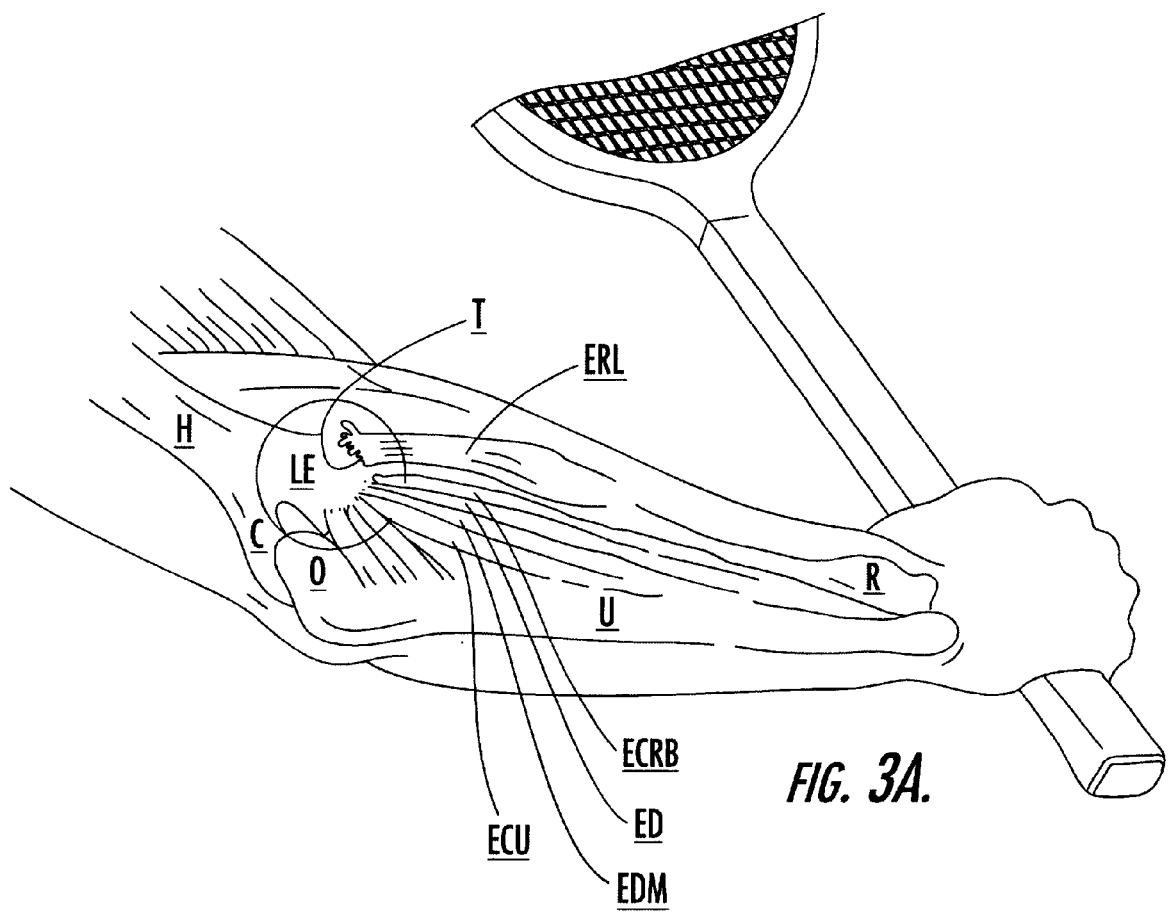
FIG. 3A is a cut-away perspective view of the right elbow and forearm of a human showing the muscles and tendons connected thereto and affected by lateral epicondylitis.
Figure 3B:
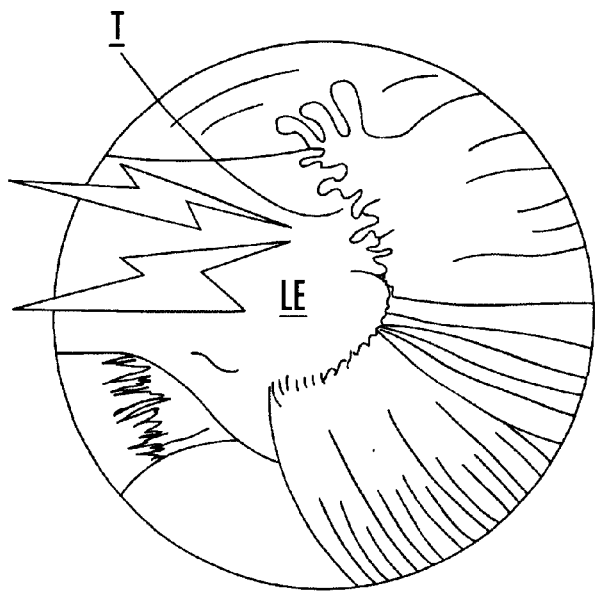
FIG. 3B is a cut-away perspective view of the elbow shown in FIG. 3A illustrating the inflamed tendons and muscles affected by lateral epicondylitis.

Referring now to FIGS. 2, 3A and 3B, the anatomy affected by lateral epicondylitis is shown. FIG. 2 shows the underlying bone and joint structure of a right elbow of a human during flexion. The elbow is formed by the junction of the capitulum "C", medial epicondyle (not shown) and lateral epicondyle "LE" of the humerus "H" with the head "HD" and olecranon "O" of the radius "R" and ulna "U", respectively. The points at which the radius "R", ulna "U" and humerus "H" meet form threejoints: the radio-humeral joint "RHJ", the humero-ulnar joint "HUJ", and the radio-ulnar joint "RUJ". As is shown in FIG. 3A, lateral epicondylitis arises from the degneration and tearing of the superficial muscles along the common tendon attachment "T" where the muscles originate at the lateral epicondyle "LE". These muscles include the extensor carpi radialis longus "ERL", the extensor carpi radialis brevis "ERB", the extensor digitorium "ED", the extensor digiti minimi "EDM", and the extensor carpi ulnaris "ECU". The supinator longus and brevis (not shown), which also originate at the lateral epicondyle, are likewise vulnerable to the degeneration and tearing associated with lateral epicondylitis.

FIG. 3B shows a detailed view of the tearing which occurs along the common tendon attachment "T" as a result of lateral epicondylitis. Without proper diagnosis and treatment, the pain initially felt by the stressed and torn tendons can be exacerbated by subperiosteal hemorrhage, periostits, calcification, and spur formation on the lateral epidcondyle. Such complications may be avoided through early diagnosis and treatment that incorporates the tennis elbow band assembly 10 of the present invention.

Figure 4:
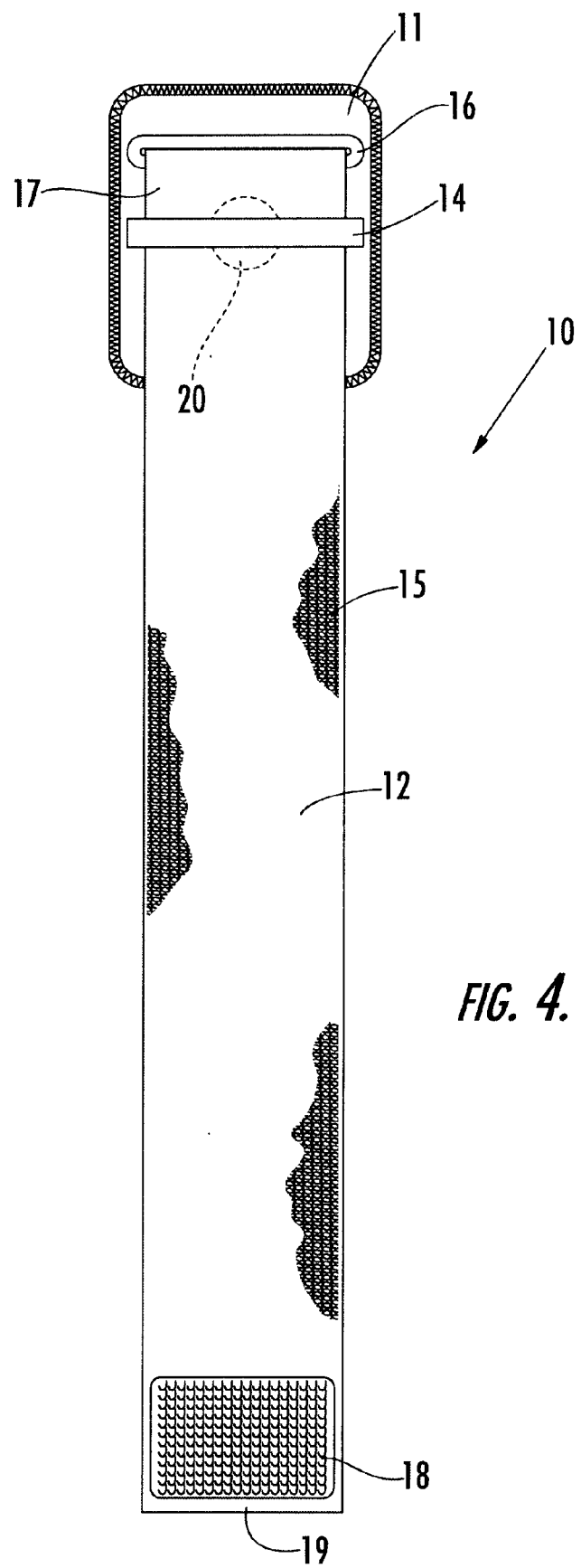
FIG. 4 is a top plan view of the tennis elbow pad assembly.

Referring now to FIG. 4, the manner in which the strap 12 is attached to the pad 11 is shown. A second patch of hook material 20 is attached to the center of the pad 11, and cooperates with the fiberous covering 15 to releasably attach the strap 12 to the pad 11. Using the patch of hook material 20 permits the pad 11 to be custom-fitted to a wearer's forearm prior to connecting the strap 12 to the pad 11.

Figure 5:
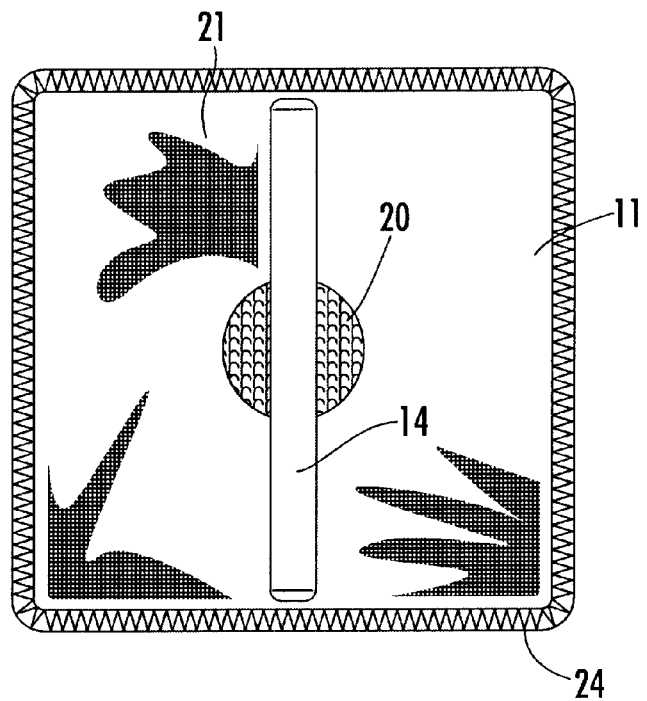
FIG. 5 is a top plan view of the tennis elbow pad shown in FIG. 4 with the strap removed.
Figure 6:
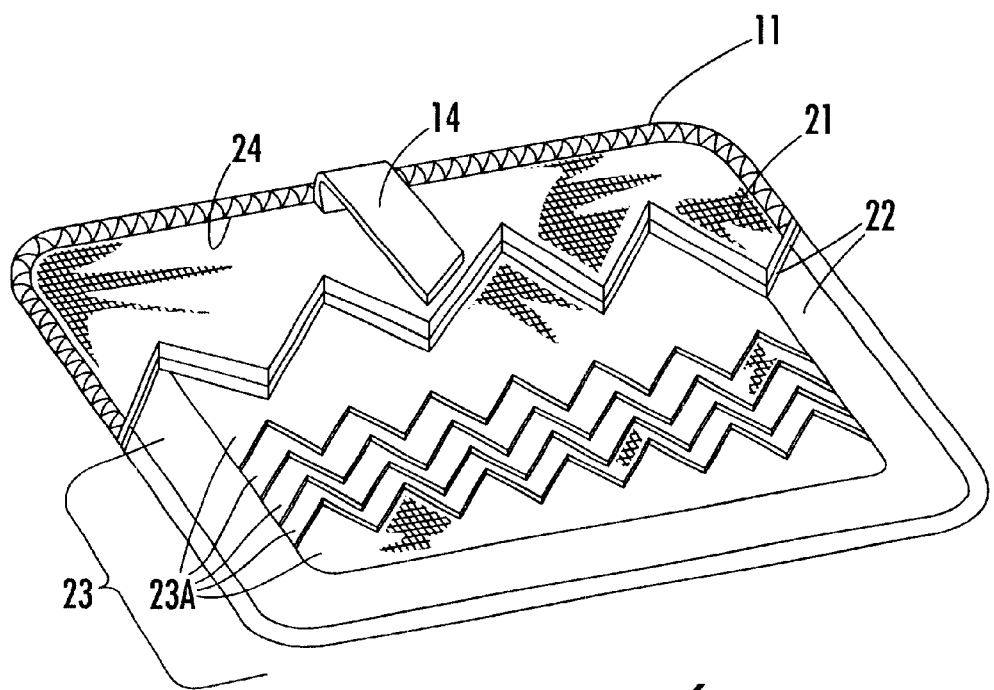
FIG. 6 is a cut-away perspective view of the tennis elbow pad shown in FIG. 5 showing the layers of substrate and other materials from which the pad is fabricated.

Referring now to FIGS. 5 and 6, the materials used to construct the pad 11 are shown. FIG. 5 shows the pad 11 prior to being custom-fitted around a wearer's forearm and with the strap 12 removed. An outer layer 21 of the pad 11 is formed from a fabric casing to which the loop 14 is sewn. Although any suitable fabric may be used, the outer layer 21 is preferably formed from polyester sheeting.

Figure 7:
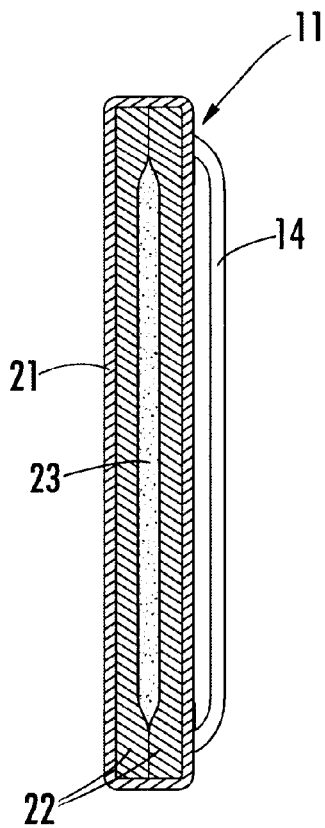
FIG. 7 is a cross-sectional side view of the tennis elbow pad showing the substrate layers and other materials of the pad bonded together.

As is shown in FIG. 6, a flexible cushion layer 22 is provided for being placed closest to the forearm. Cushion layer 22 is preferably laminated, four pound ethylene vinyl acetate ("EVA") micro-perf closed cell foam having a thickness of ⅛ inch. The cushion layer 22 provides a padded, comfortable surface next to the skin, with the EVA being flexible enough to bend easily with the other components of the pad 11. An initially flexible inner layer 23 is positioned within cushion layer 22. The inner layer 23 is preferably formed from fiberglass fabric layers 23A, each of which is impregnated with a moisture-curable resin that hardens upon curing to form a rigid structure which retains the shape of the muscles and tendons of the forearm onto which the pad 11 has been molded. Although any suitable number of fabric layers 23A may be used, the inner layer 23 preferably includes three to five fabric layers 23A. The embodiment of the invention shown in FIG. 6 includes five fabric layers 23A. FIG. 7 shows the inner layer 23 sandwiched between the cushion layer 22 and the outer layer 21 after the pad 11 has been assembled.

Each fiberglass fabric layer 23A is impregnated or coated with a moisture-curable resin such as polyisocyanate. This resin is described in full in the present Applicant's U.S. Pat. No. 4,770,299. The resin is synthesized using a reactive system that remains stable when maintained in substantially moisture-free conditions, yet hardens upon exposure to sufficient moisture to form a rigid, self-supporting structure. A typical formation of the reactive system is as follows:

| Typical Formulation | | | |
|---|---|---|---|
| Isonate↓ 143L | or | | |
| Mondur↓ CD | or | polyisocyanate | 50.0% |
| Rubinate ↓ X1168 | | | |
| Pluracol↓ P1010 | | polyol | 46.6% |
| DC-200 Silicone | | defoaming agent | 0.30% |
| Benzoyl Chloride | | stabilizer | 0.10% |
| Thancat↓ DM-70 | | catalyst | 3.0% |
| | | | 100% |

The polyisocyanate resin remains in a viscous state as long as the resin is not exposed to moisture. This permits the substrate to remain flexible and moldable so long as the resin is not exposed to moisture, and for a short period of time after such exposure occurs. The rate at which the resin cures can be controlled to some extent by the quantity of water to which the resin is exposed. Briefly immersing the resin in water will cause the resin to rapidly cure. In contrast, merely exposing the resin to open air will result in a curing process having a significantly slower reaction rate which will be proportional to the amount of moisture in the air to which the resin is exposed.

The individual fiberglass fabric layers 23A are preferably die-cut to shape. In addition, while each fabric layer 23A preferably has the same width, a different width may be used for each layer 23A. The degree of overlap and non-overlap resulting from the varying widths provides a variable thickness across the pad 11 after curing, with a relatively thick predetermined area where increased rigidity is desired and a relatively thin area where increased flexibility is desired. The manner of varying the widths of the fabric layers 23A is described in detail in Applicant's prior U.S. Pat. No. 5,755, 678.

Although the fabric layers 23A are preferably formed from fiberglass, the inner layer 23 may alternately be formed from a fabric woven or knitted from polypropylene yarns. Such fabric is somewhat more flexible than fiberglass fabric after hardening, and offers some cost savings during production of the pad assembly 10.

Referring again to FIG. 5, the fabric outer layer 21 and the cushion layer 22 are joined around the perimeter by overedge sewing stitches 24. Although the outer fabric layer 21 and cushion layer 22 may be sewn together using an overedge or serging seam, because the outer layer 21 and cushion layer 22 have thermoplastic properties, the outer layer 21 and cushion layer 22 may alternatively be bonded together around the edge using radio-frequency ("RF") welding. RF welding is a particularly efficient method of bonding because it permits tight corners and angles to be formed in the pad 11, some of which cannot be formed using conventional sewing techniques. The inner layer 23 may alternatively be enclosed between the cover 12 and pad 13 using ultrasonic sealing or other suitable adhesives.

Figure 8:
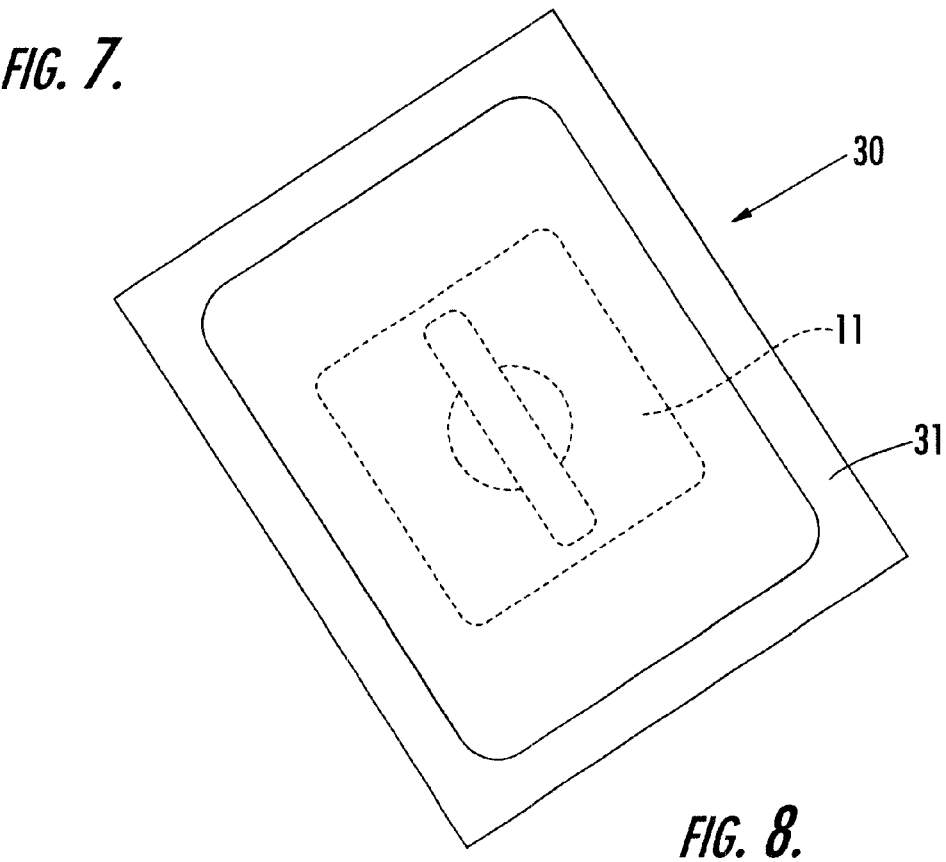
FIG. 8 is a top plan view of a tennis elbow pad product according to another embodiment of the invention.

Referring now to FIG. 8, a tennis elbow pad product is illustrated and shown generally at reference numeral 30. The pad product 30 includes an outer moisture-impervious foil and laminated pouch 31 in which the pad 11 is sealed in the absence of moisture. The pouch 31 is preferably formed from a 0.5 mil aluminum foil sheet sandwiched between two layers of low density polyethylene film. Each layer of film preferably has a thickness of 2 mils. The pouch 31 may also include an outermost layer of laminated 60 gauge, bi-axially oriented nylon film. When the pouch 31 is properly sealed, this laminate structure will prevent moisture from entering the pouch indefinitely.

Figure 9:
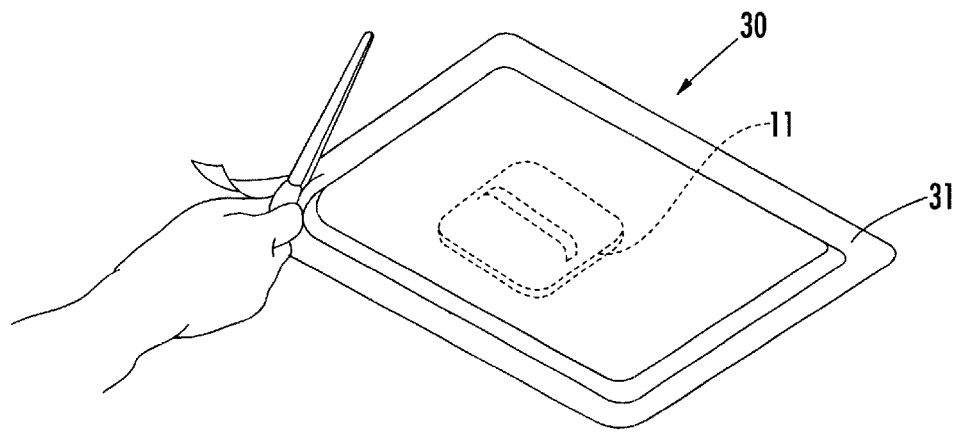
FIG. 9 is a perspective view of the tennis elbow pad product shown in FIG. 8 showing the tennis elbow pad being removed from a moisture-impervious pouch by opening the pouch immediately prior to initiating the curing and custom-fitting process.
Figure 10:
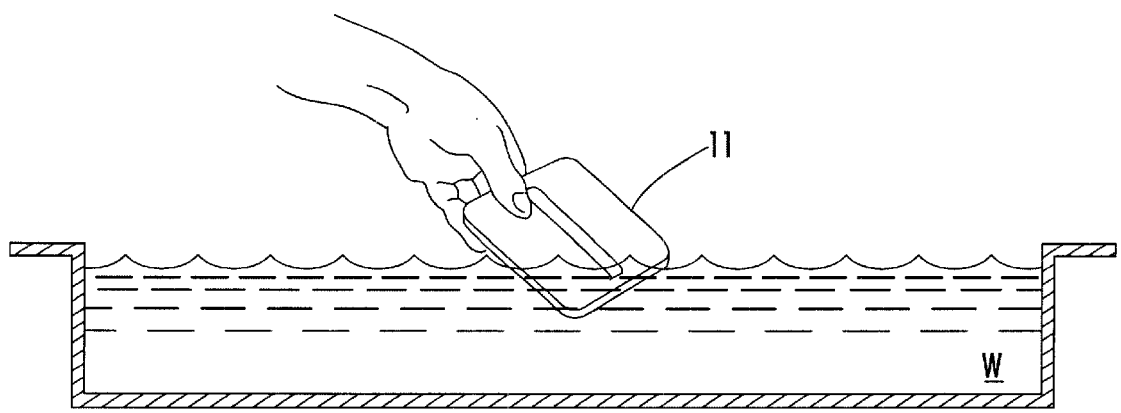
FIG. 10 illustrates activation of the moisture-curable resin in the tennis elbow pad.

Referring now to FIG. 9, the moisture-impervious pouch 31 may be opened with scissors or a knife so that the pad 11 can be removed from the pouch 31. FIG. 10 shows the pad 11 after removal from the pouch 31 being immersed in water "W" to activate the curing process.

Figure 11:
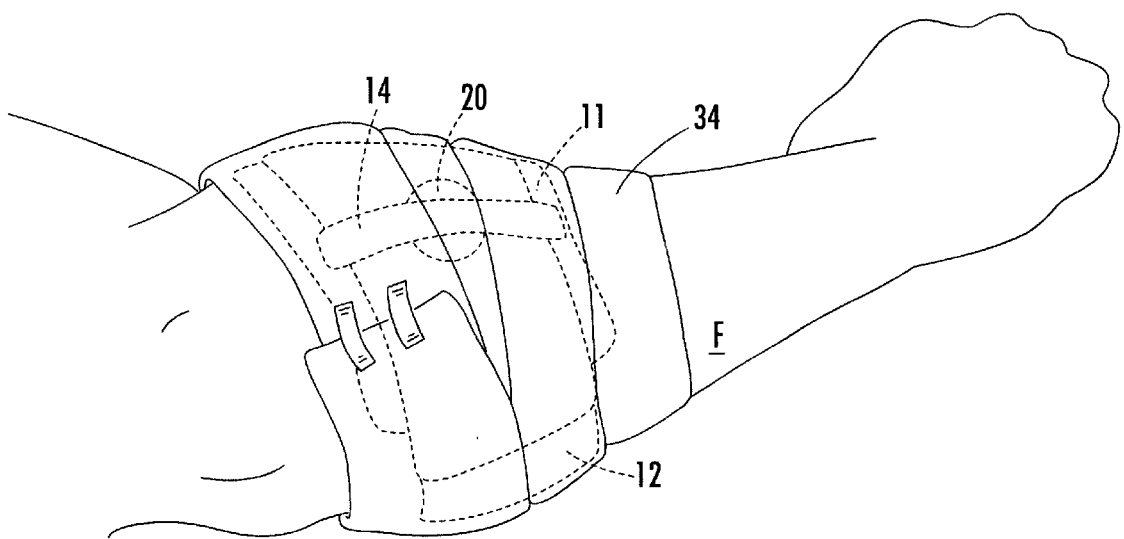
FIG. 11 is an environmental perspective view showing the tennis elbow pad assembly being custom-fitted to the forearm of a wearer.
Figure 12:
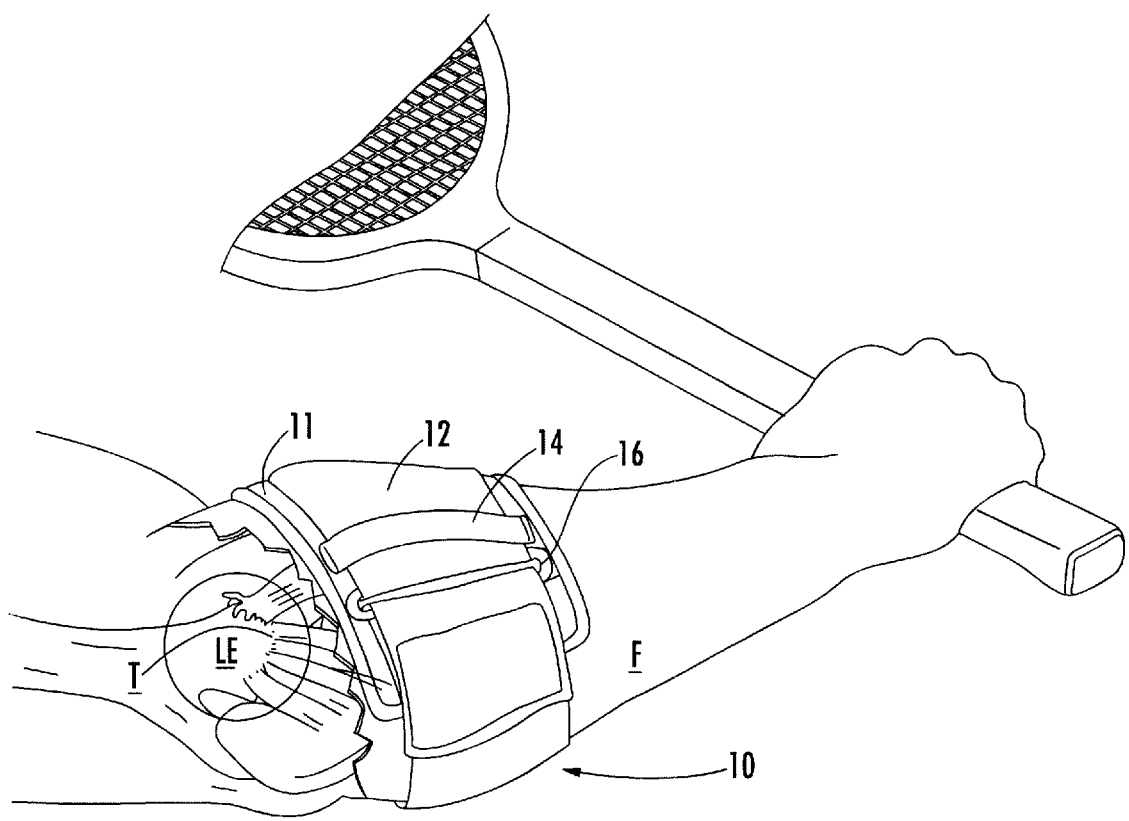
FIG. 12 is a cutaway environmental perspective view showing the tennis elbow pad assembly in use after the curing process has been completed.

As is shown in FIG. 11, the pad 11 is then positioned on the forearm over the inflamed area and the strap 12 is attached to the patch of hooked material 20. The strap 12 is wrapped around the forearm "F" and loosened or tightened as needed to ensure a correct fit. The forearm "F" is then overwrapped with an elastic bandage 34, which remains around the forearm "F" for a period of time sufficient to allow the resin in or on the pad 11 to harden and form the pad 11 into the desired conformation against the forearm "F". The patient must be advised not to attempt to flex or extend the elbow during the curing process to ensure that an accurate custom fit is achieved. Once the curing process is completed, the elastic bandage 34 is removed. FIG. 12 shows the fully cured tennis elbow pad assembly 10 positioned around the forearm "F", with the custom-fitted pad 11 cooperating with the strap 12 to exert radially-directed pressure against the muscles and common tendon attachment "T" originating at the lateral epicondyle to provide relief from the pain associated with lateral epicondylitis.

Throughout this specification, the tennis elbow pad assembly 10 is described for use in relieving the symptoms of lateral epicondylitis. However, the pad assembly 10 may alternatively be used to relieve the symptoms of medial epicondylitis, or "golfer's elbow", by custom-fitting the pad 11 over the muscles and tendons originating at the medial epicondyle.

One preferred embodiment of the tennis elbow pad assembly 10 has the following specifications:

| | |
|---|---|
| Length of pad 11 | 2 inches |
| Width of pad 11 | 2 inches |
| Length of loop 14 | 1.5 inches seam-to-seam |
| Diameter of patch of hooked material 20 | .5 inch |
| Width of strap 12 | 2 inches |

| -continued | |
|---|---|
| Length of strap 12 | 17 inches |
| Outer layer 21 | Polyester sheeting |
| Cushion layer 22 | .25 inch microperf EVA closed cell foam |
| Number of fiberglass layers 23A | 5 |
| Bandage 34 | 2 inch x 5 yard stretch elastic-free elastic bandage |

A tennis elbow pad assembly is described above. Various details of the invention may be changed without departing from its scope. Furthermore, the foregoing description of the preferred embodiment of the invention and the best mode for practicing the invention are provided for the purpose of illustration only and not for the purpose of limitation-the invention being defined by the claims.

I claim:

1. A tennis elbow pad assembly product for relieving the symptoms of lateral epicondylitis, comprising:
   (a) an outer pouch formed of a moisture-imparvious material;
   (b) a pad positioned in said pouch in substantially moisture-free conditions and sealed therein against entry of moisture until use, and adapted for being positioned against and molded onto a forearm in the region of the elbow for lying in a closely-conforming position against and applying radially-directed pressure to the common tendon attachment and grasping and supination muscles associated with the radial-humeral joint and the lateral epicondyle of the forearm and hardened into a rigid structure for being compressed against the forearm in the region of the elbow for alleviating pain associated with lateral epicondylitis without provision of protection to the forearm in the region of the elbow, said pad comprising:
      (i) an initially flexible substrate impregnated of coated with a reactive system, said system remaining stable when maintained in substantially moisture-free conditions and hardening upon exposure to moisture to form a rigid, self-supporting structure having a shape conforming to the forearm to which the pad is molded during curing;
      (ii) a cushion layer overlying at least two sides of said substrate; and
      (iii) a flexible outer layer overlying at least one side of the substrate; and
   (c) a support cooperating with the pad for maintaining the pad in the closely-conforming position against the forearm.

2. A tennis elbow pad assembly product according to claim 1, wherein said support comprises an elongate strap having an outer surface and first and second ends, wherein said first end of the strap is releasably attached to an upper surface of the pad, thereby permitting the strap to extend around the forearm for securing the pad in the closely conforming configuration against the forearm.

3. A tennis elbow pad assembly product according to claim 1 or 2, wherein said outer pouch is formed of a laminated structure having at least one layer of plastic film and at least one layer of aluminum foil bonded to said plastic film.

4. A tennis elbow pad assembly product according to claim 1 or 2, wherein said substrate comprises a plurality of overlaid thicknesses of fiberglass.

5. A tennis elbow pad assembly product according to claim 4, wherein said plurality of thicknesses comprises at least three and no more than five thicknesses.

6. A tennis elbow pad assembly according to claim 4, wherein said cushion layer comprises foam.

7. A tennis elbow pad assembly product according to claim 6, wherein said foam is selected from the group consisting of closed-cell ethylene vinyl acetate and polyurethane.

8. A tennis elbow pad assembly product according to claim 1 or 2, wherein said reactive system comprises a blended polyisocyanate, polyol, catalyst and stabilizer.

9. A tennis elbow pad assembly product according to claim 2, and including a loop attached to said upper surface and adapted for receiving the strap therethrough for securing the pad against the forearm.

10. A tennis elbow pad product according to claim 9, and including a first fastener attached to the upper surface for cooperating with a complementary inner surface of the strap for holding the pad in place on the forearm while being worn.

11. A tennis elbow pad assembly product according to claim 10, wherein said first fastener comprises a patch of hook-and-loop material complementary to said inner surface.

12. A tennis elbow pad assembly product according to claim 11, wherein said first end of the strap includes a fastening ring connected thereto and adapted for receiving said second end therethrough for securing the strap around the forearm.

13. A tennis elbow pad assembly product according to claim 12, and including a second fastener attached to the second end of the strap for being releasably connected to said outer surface, thereby permitting the strap to be secured around the forearm.

14. A tennis elbow pad assembly product according to claim 13, wherein said outer surface of the strap comprises hook-and-loop material.

15. A tennis elbow pad assembly product according to claim 14, wherein said second fastener comprises a patch of hook-and-loop material complementary to the outer surface.

16. A tennis elbow pad assembly product according to claim 1, wherein said outer layer further comprises a flexible protective cover enclosing said cushion layer, wherein the substrate, cushion layer and cover are joined together to form a unitary structure for being molded while flexible to an aspect of the forearm and elbow.

17. A tennis elbow pad assembly product according to claim 16, wherein said cover is formed of a polyester sheeting fabric.

18. A tennis elbow pad assembly for relieving the symptoms of lateral epicondylitis, comprising:
  (a) a pad adapted for being positioned against and molded onto a forearm in the region of the elbow to harden into a rigid shape for lying in a closely-conforming position against and applying radially-directed pressure to the common tendon attachment and grasping and supination muscles associated with the radial-humeral joint and the lateral epicondyle of the forearm and hardened into a rigid structure for being compressed against the forearm in the region of the elbow for alleviating pain associated with lateral epicondylitis without provision of protection to the forearm in the region of the elbow, said pad comprising:
    (i) an initially flexible inner substrate impregnated or coated with a reactive system, said system remaining stable when maintained in substantially moisture-free conditions and hardening upon exposure to moisture to form a rigid, self-supporting structure having a shape conforming to the forearm to which the pad is molded during curing;
    (ii) a cushion layer enclosing at least two sides of said substrate; and
    (iii) a flexible cover enclosing said cushion layer; and
  (b) a support cooperating with said pad for maintaining the pad in its closely-conforming position against the forearm.

19. A tennis elbow pad assembly according to claim 18, wherein said support comprises an elongate strap having an outer surface and first and second ends, wherein said first end of the strap is releasably attached to an upper surface of the pad, thereby permitting the strap to extend around the forearm for securing the pad in the closely conforming configuration against the forearm.

20. A tennis elbow pad assembly according to claim 18 or 19, wherein said substrate comprises a plurality of overlaid thicknesses of fiberglass.

21. A tennis elbow pad assembly according to claim 20, wherein said plurality of thicknesses comprises at least three and no more than five layers.

22. A tennis elbow pad assembly according to claim 20, wherein said cushion layer comprises foam.

23. A tennis elbow pad assembly product according to claim 22, wherein said foam is selected from the group consisting of closed-cell ethylene vinyl acetate and polyurethane.

24. A tennis elbow pad assembly product according to claim 22, wherein the substrate, foam layer and cover are joined together to form a unitary structure for being molded while flexible to an aspect of the forearm and elbow.

25. A tennis elbow pad assembly according to claim 24, wherein said cover is formed of a polyester sheeting fabric.

26. A tennis elbow pad assembly according to claim 18 or 19, wherein said reactive system comprises a blended polyisocyanate, polyol, catalyst and stabilizer.

27. A tennis elbow pad assembly according to claim 19, and including a loop attached to said upper surface and adapted for receiving the strap therethrough for securing the pad against the forearm.

28. A tennis elbow pad according to claim 27, and including a first fastener attached to the upper surface for cooperating with a complementary inner surface of the strap for holding the pad in place on the forearm while being worn.

29. A tennis elbow pad assembly according to claim 28, wherein said first fastener comprises a patch of hook-and-loop material complementary to said inner surface.

30. A tennis elbow pad assembly according to claim 29, wherein said first end of the strap includes a fastening ring connected thereto and adapted for receiving said second end therethrough for securing the strap around the forearm.

31. A tennis elbow pad assembly according to claim 30, and including a second fastener attached to the second end of the strap for being releasably connected to said outer surface, thereby permitting the strap to be secured around the forearm.

32. A tennis elbow pad assembly according to claim 31, wherein said outer surface of the strap comprises hook-and-loop material.

33. A tennis elbow pad assembly according to claim 32, wherein said second fastener comprises a patch of hook-and-loop material complementary to the outer surface.

* * * * *

UNITED STATES PATENT AND TRADEMARK OFFICE
CERTIFICATE OF CORRECTION

PATENT NO. : 6,478,760 B2 Page 1 of 1
DATED : November 12, 2002
INVENTOR(S) : Thomas D. Darcey It is certified that error appears in the above-identified patent and that said Letters Patent is hereby corrected as shown below:

<u>Column 8,</u>
Line 21, delete "imparvious" and insert -- impervious --.
Line 36, delete "of" and insert -- or --.

Signed and Sealed this

Second Day of September, 2003

JAMES E. ROGAN
*Director of the United States Patent and Trademark Office*